United States Patent [19]

Ogle

BEST AVAILABLE COPY

[11] E Re. 29,062

[45] Reissued Dec. 7, 1976

[54] INTRAVENOUS CONTAINER MIXING ASSEMBLY

[75] Inventor: Robert W. Ogle, Newport Beach, Calif.

[73] Assignee: IMS Limited, S. El Monte, Calif.

[22] Filed: June 16, 1975

[21] Appl. No.: 587,151

Related U.S. Patent Documents

Reissue of:

[64] Patent No.: 3,858,580
Issued: Jan. 7, 1975
Appl. No.: 302,783
Filed: Nov. 1, 1972

U.S. Applications:

[60] Continuation-in-part of Ser. No. 195,886, Nov. 4, 1971, which is a division of Ser. No. 830,311 June 4, 1969, Pat. No. 3,674,028.

[52] U.S. Cl. ..... 128/214 C; 128/221; 222/81

[51] Int. Cl.[2] ..... A61M 5/16

[58] Field of Search ..... 128/218 M, 272, 221, 128/DIG. 28, 214 R, 214 C, 214.2, 215; 215/6; 206/47 A; 222/81

[56] References Cited

UNITED STATES PATENTS

| | | | |
|---|---|---|---|
| 2,111,985 | 3/1938 | Meyer | 215/6 X |
| 2,232,978 | 2/1941 | Smith | 128/DIG. 28 |
| 2,377,274 | 5/1945 | Smith | 128/218 M |
| 2,610,628 | 9/1952 | Lockhart | 128/DIG. 28 |
| 3,467,097 | 9/1969 | Ogle | 128/DIG. 28 |
| 3,494,359 | 2/1970 | Zackheim | 128/218 M |
| 3,670,728 | 6/1972 | Dabney | 128/214 C |

FOREIGN PATENTS OR APPLICATIONS

| | | | |
|---|---|---|---|
| 1,071,557 | 3/1954 | France | 128/214 C |
| 1,225,859 | 7/1960 | France | 128/214 C |
| 66,274 | 3/1956 | France | 128/214 C |

*Primary Examiner*—John D. Yasko
*Attorney, Agent, or Firm*—Wills, Green & Mueth

[57] ABSTRACT

A device for the mixing and administration of intravenous fluid comprising a cylindrical vial having an open end and a closed end, an inwardly extending integral annular ring within the vial and forming part of the walls of the vial intermediate said open and closed ends. A tippable center septum seals on the annular ring. An imperforate stopper is provided in the open end of the vial. The vial is adapted to contain two liquids or a liquid and a dry material in separated state. A non-opaque drip meter having a fluid outlet at one end and a fluid inlet is provided, the inlet comprising a tubular member terminating within the drip meter whereby drops can be visually observed at the end of the tubular member through the drip meter. Extending from the drip meter is a solid or hollow elongated rigid spike having an enlarged base adjacent the drip meter, the spike terminating in a point at its other end. A filtered air inlet is positioned in proximity to the base of the spike, a passage and filter are associated with the spike or base for admitting filtered air into the vial. A fluid passage runs through the base and has one end adjacent the spike at the exterior of the base and the other end communicates with the tubular member. The spike is adapted to puncture the stopper and tip the septum whereby the contents of the vial can be mixed without contamination from the exterior and the fluid contents of the vial can flow through the fluid passage and the drip meter while filtered air passes into the vial.

10 Claims, 8 Drawing Figures

INTRAVENOUS CONTAINER MIXING ASSEMBLY

Matter enclosed in heavy brackets [ ] appears in the original patent but forms no part of this reissue specification; matter printed in italics indicates the additions made by reissue.

This application is a continuation-in-part of application Ser. No. 195,886, filed Nov. 4, 1971, which was a divisional application of application Ser. No. 830,311, filed June 4, 1969 and now issued as U.S. Pat. No. 3,674,028.

BACKGROUND OF INVENTION

Various intravenous solution sets are known in the prior art. In general, these devices involve the drip meter assembly which has a sharp puncturing member at its upper end for piercing the stopper of a bottle of intravenous solution. The puncturing member normally has associated therewith an air inlet and a fluid outlet. Many medicaments must be stored and packaged in a dry or lyophilized state, and require reconstitution with a liquid diluent just prior to use. Heretofore, the reconstitution of such materials for administration in an intravenous set required the nurse or technician to make one or more transfers of diluent in an open and uncontrollable manner. This procedure carries with it the grave risk of bacterial contamination. It also creates the chance of a mistake occurring as the result of a mix-up of solution bottles. The present invention is basically concerned with eliminating these problems and hazards by providing a closed system in which the solid medicament and its diluent can be packaged under strict sterile conditions at the factory, and reconstituted at the time of use without the necessity of the medicament becoming contaminated during a transfer operation. It is believed that this invention involves a major advance in the art of administering intravenous solutions.

SUMMARY OF THE INVENTION

Briefly, this invention comprises a novel device for the mixing and administration of intravenous fluid comprising a cylindrical vial having an open end and a closed end, an inwardly extending integral annular ring within said vial and forming part of the walls of said vial intermediate said open and closed ends, a tippable center septum sealing on said annular ring, an imperforate stopper in said open end, said vial being adapted to contain two liquids or a liquid and a dry material in separated state, a non-opaque drip meter having a fluid outlet at one end and a fluid inlet, said inlet comprising a tubular member terminating within said drip meter whereby drops can be visually observed at the end of said tubular member through said drip meter, extending from said drip meter a solid or hollow elongated rigid spike having an enlarged base adjacent said drip meter, said spike terminating in a point at its other end, a filtered air inlet positioned in proximity to the base of said spike, means associated with said spike or base for admitting filtered air into said vial, a fluid passage running through said base and having one end adjacent the spike at the exterior of said base and the other end communicating with said tubular member, said spike being adapted to puncture said stopper and tip said septum whereby the contents of the vial can be mixed without contamination from the exterior and the fluid contents of said vial can flow through said fluid passage and said drip meter while filtered air passes into said vial.

It is an object of my invention to provide a novel device for the administration of intravenous fluids.

More particularly, it is an object of this invention to provide a novel device which is adapted for the administration and reconstitution of medicament in a completely closed system.

Another object of this invention is to provide a novel device for the packaging and administration of medicament for intravenous use which during storage is maintained in separated condition; viz, two liquids or a liquid and a dry material.

These and other objects and advantages of this invention will be apparent from the detailed description which follows.

DESCRIPTION OF PREFERRED EMBODIMENTS

Turning to the drawings.

Figure 2:
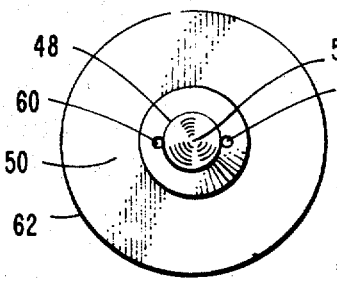
FIG. 2 is a top view of the device of FIG. 1.

Considering the drawings in greater detail, the cylindrical vial 10 has an open end 12 and a closed end 14. The center septum 16 is positioned just above and abuts the integral annular ring 18. Below ring 18 is chamber 20 which contains a dry or lyophilized medicament 22. The septum 16 has four sealing rings 24, 26, 28 and 30 which form a seal on the inside walls of the vial 10. A chamber 32 for liquid or diluent 34 is provided between septum 16 and the end stopper 36. The end stopper 36, unlike septum 16, is non-reciprocating; that is, it is not slidable downwardly within vial 10, such movement being prevented by shoulders 38 which overlay and may seal upon the ends of vial 10.

The drip meter 40 has an outlet 42 provided with tubing 44 normally intended to carry the intravenous solution to the patient in conventional fashion. The drip meter 40 is normally non-opaque; that is, transparent or translucent so that drops of fluid may be observed and/or counted. The drip meter 40 has a fluid inlet comprising a tubular member 46 which terminates within the non-opaque drip meter. In FIGS. 1–7, the rigid spike 48 is solid and has an enlarged base 50 adjacent the drip meter 40. The spike 48 has a point 52 at one end. The opening 54 in base 50 communicates with air opening 56. The opening 56 is normally provided with cotton 58 or other filtering material intended to entrap any airborne particulate matter or bacteria in the entering air. The fluid passage 60 runs through the base 50 and functions as a downcomer for fluid. The lower end of passage 60 communicates with the tubular member 46.

Figure 1:
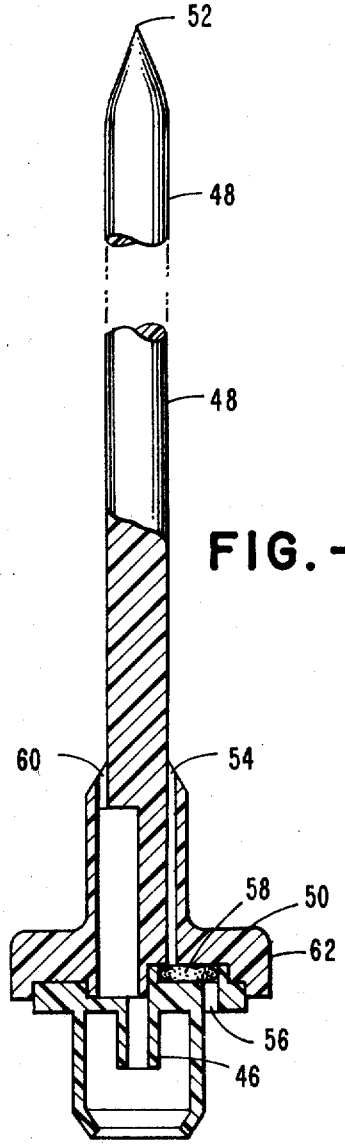
FIG. 1 shows one embodiment of the drip meter and spike of this invention.
Figure 4:
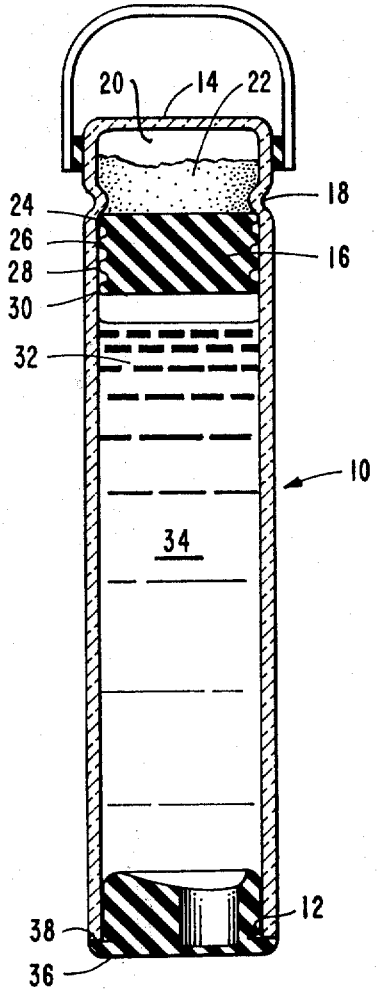
FIG. 4 shows, in side sectional view, one embodiment of the vial, center septum and end stopper of this invention.
Figure 3:
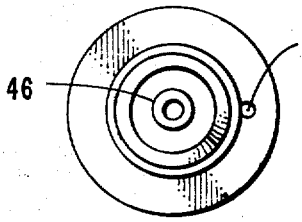
FIG. 3 is a bottom view of the device of FIG. 1.
Figure 5:
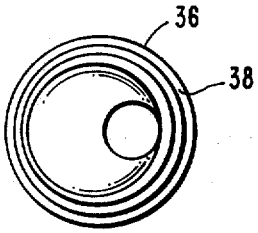
FIG. 5 is a plan view of the end stopper of the vial of FIG. 4.
Figure 6:
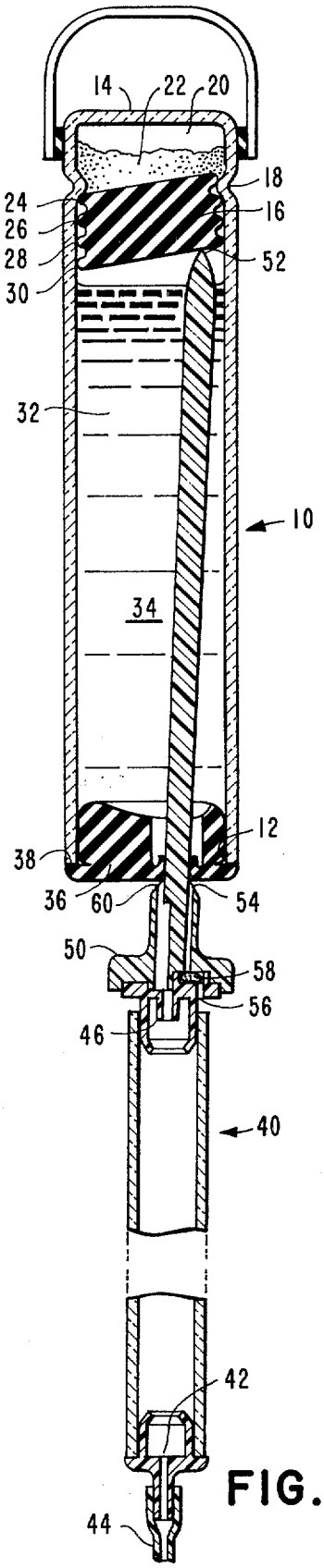
FIG. 6 shows, in sectional view, the parts of FIGS. 1–5 in partially assembled condition.
Figure 7:
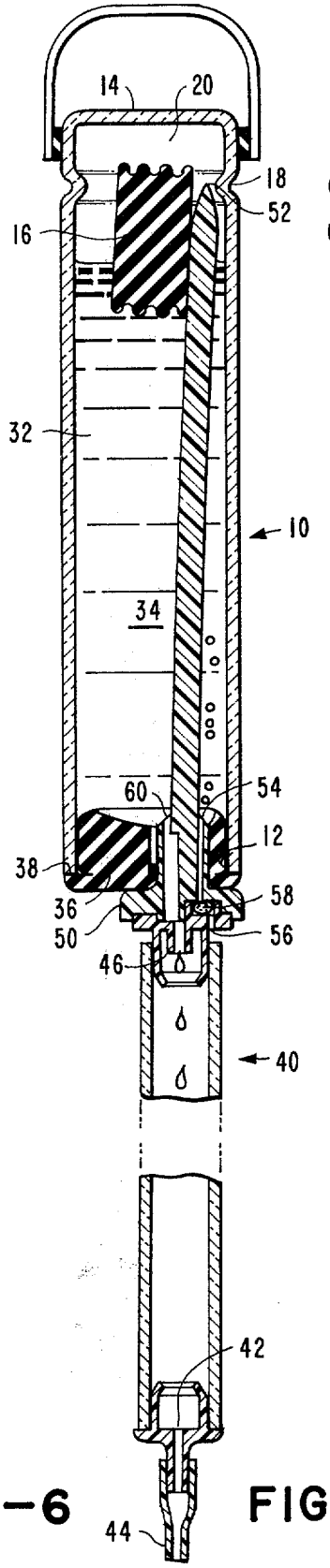
FIG. 7 is a sectional view of the parts of FIGS. 1–5 in fully assembled condition.

In use, the parts shown in FIGS. 1 and 2 are made up beginning as in FIG. 6 and concluding as in FIG. 7 whereby the spike 48 tips the center septum 16, allowing mixing and reconstitution to occur. The flange 62 is brought up flush with the exterior of stopper 36 so that passage 60 is in fluid communication with the fluid contents of the vial 10. The spike 48 is long enough to reach and tip septum 16 at or prior to the time the flange 62 is flush with stopper 36.

Figure 8:
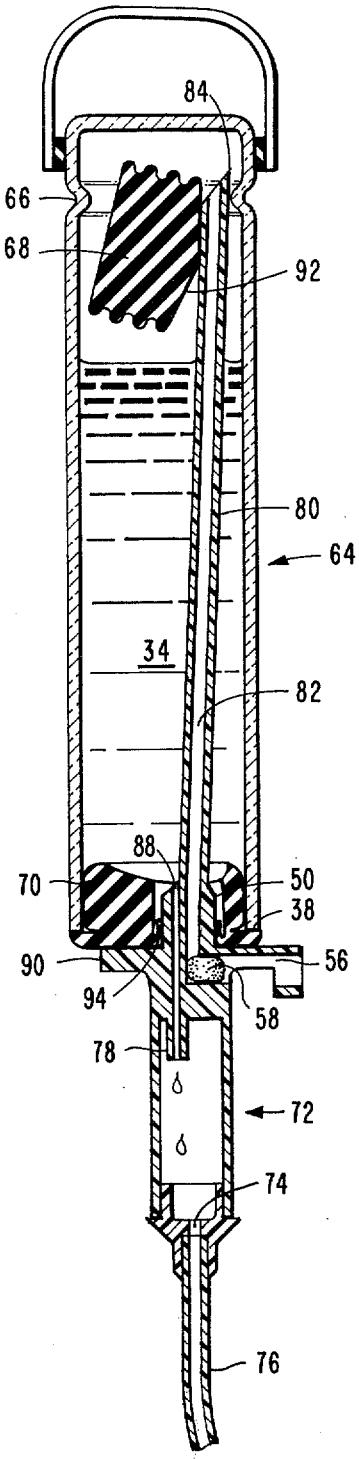
FIG. 8 is a sectional view of another embodiment of this invention.

FIG. 8 shows another embodiment of this invention wherein the vial 64, annular ring 66, center septum 68 and end stopper 70 have the structure previously described. The drip meter 72 has an outlet 74 provided with tubing 76 and a fluid inlet comprising the tubular member 78. In this embodiment, the rigid spike 80 is hollow and has a central opening 82 and a scarf or point 84 at one end. The opening 82 communicates with the air opening 86. The fluid passage 88 runs through the base 90 and communicates with tubular member 78. In this embodiment the point 84 is above the initial fluid level in the vial 64 when the parts are fully assembled. Thus, the entering air is discharged at point 84, above the fluid level in the vial. This effectively reduces the risk of contamination of the fluid by the incoming air. Also, in FIG. 8 the septum 68 has a centrally domed surface 92 which facilitates the tipping of the septum by the spike 80. The domed surface is particularly desirable where the spike is centrally disposed in the vial rather than offset from the centerline of the vial as shown in the drawings.

It is to be noted that the tipping action afforded by the annular ring and septum, allows the chamber adjacent the closed end of the vial to be smaller than the diameter of the septum. In other words, by providing for tipping action, this chamber can be substantially reduced in length since it does not receive the septum in length. This function reduces glass usage and saves space.

Preferably, the end stopper has a circular area bridged by a thin imperforate diaphragm 94. The diaphragm is readily punctured by the point of the spike.

Having fully described the invention, it is intended that it be limited only by the scope of the appended claims.

I claim:

1. A novel device for the administration of intravenous fluids which comprises a cylindrical fluid container having an open end and a closed end, an imperforate stopper in said open end, an annular inwardly projecting ring within said container, a tippable center septum abutting said ring, a non-opaque drip meter having a fluid outlet at one end and a fluid inlet, said inlet comprising a tubular member terminating within said drip meter whereby drops can be visually observed at the end of said tubular member through said drip meter, extending from said drip meter an elongated rigid spike having an enlarged base adjacent said drip meter, said spike terminating in a point at its other end, said other end extending into said container, a filtered air inlet positioned in proximity to the base of said spike, means for admitting filtered air into said container, a fluid passage running through said base and having one end adjacent the spike at the exterior of said base so that essentially all of the fluid within said container can drain out by gravity through said fluid passage, and the other end of said fluid passage communicating with said tubular member, the point of said spike being adapted to puncture said stopper and tip said septum whereby contents of said container can be mixed without contamination from the exterior and the fluid contents can flow through said fluid passage and drip meter while filtered air passes into said vial.

2. A novel device for the administration of intravenous fluids which comprises a cylindrical fluid vial having an open end and a closed end, an imperforate stopper in said open end, an annular inwardly projecting ring within said vial, a tippable center septum abutting said ring, a non-opaque drip meter having a fluid outlet at one end and a fluid inlet, said inlet comprising a tubular member terminating within said drip meter whereby drops can be visually observed at the end of said tubular member through said drip meter, extending from said drip meter an elongated rigid solid spike having an enlarged base adjacent said drip meter, said solid spike terminating in a point at its other end, said other end extending into said container, a filtered air inlet positioned in proximity to the base of said solid spike, means for admitting filtered air into said container, a fluid passage running through said base and having one end adjacent the solid spike at the exterior of said base so that essentially all of the fluid within said container can drain out by gravity through said fluid passage, and the other end of said fluid passage communicating with said tubular member, the point of said solid spike being adapted to puncture said stopper and tip said septum whereby contents of said vial can be mixed without contamination from the exterior and the fluid contents can flow through said fluid passage and drip meter while filtered air passes into said vial.

3. The device of claim 2 wherein said solid spike is offset from the centerline of said vial.

4. The device of claim 2 wherein said septum has a centrally domed surface facing said stopper.

5. The device of claim 2 wherein said drip meter has an external flange which abuts said end stopper.

6. The device of claim 2 wherein said end stopper is non-reciprocating.

7. The device of claim 2 wherein said chamber adjacent said closed end is shorter than the diameter of said septum.

8. The device of claim 7 wherein said septum has a plurality of rings sealing on the walls of said vial.

9. The device of claim 1 wherein said spike is hollow and has a central internal passage which communicates with said filtered air inlet.

*10. A novel device for the administration of intravenous fluids which comprises a fluid container having an open end and a closed end, an imperforate stopper in said open end, said container having two coaxial cylindrical compartments, a tippable center septum separating said compartments, a non-opaque drip meter having a fluid outlet at one end and a fluid inlet, said inlet comprising a tubular member terminating within said drip member whereby drops can be visually observed at the end of said tubular member through said drip meter, extending from said drip meter an elongated rigid spike having an enlarged base adjacent said drip meter, said spike terminating in a point at its other end, said other end extending into said container, a filtered air inlet positioned in proximity to the base of said spike, means for admitting filtered air into said container, a fluid passage running through said base and having one end adjacent the spike at the exterior of said base so that essentially all of the fluid within said container can drain out by gravity through said fluid passage, and the other end of said fluid passage communicating with said tubular member, the point of said spike being adapted to puncture said stopper and tip said septum whereby contents of said container can be mixed without contamination from the exterior and the fluid contents can flow through said fluid passage and drip meter while filtered air passes into said vial.*

* * * * *